United States Patent [19]

Korbonits et al.

[11] Patent Number: 4,565,817
[45] Date of Patent: Jan. 21, 1986

[54] THEOPHYLLINYL-ALKYL-OXADIAZOLES, PROCESS FOR THE PREPARATION THEREOF AND PHARMACEUTICAL COMPOSITIONS CONTAINING SAME

[75] Inventors: Dezsö Korbonits; Maria Szomor née Wundele; Gergely Héja, all of Budapest; Ida Szvoboda née Kanzel, Dunakeszi; Pál Kiss; Csaba Gönczi, both of Budapest; Endre Pálosi; Gábor Kovács, both of Budapest; Judit Kun, Budapest; Emil Minker, Szeged; Sándor Virág; Gyula Sebestyén, both of Budapest; Tamás Szüts, Budapest, all of Hungary

[73] Assignee: Chinoin Gyogyszer-es Vegyeszeti Termekek Gyara R.T., Budapest, Hungary

[21] Appl. No.: 474,227

[22] Filed: Mar. 11, 1983

[30] Foreign Application Priority Data

Dec. 3, 1982 [HU] Hungary ............................. 762/82

[51] Int. Cl.$^4$ .................... C07D 473/10; A61K 31/52
[52] U.S. Cl. .................................. 514/263; 544/269; 544/267; 544/138; 544/364
[58] Field of Search ............... 544/269, 266, 267, 138; 424/253; 514/364, 263

[56] References Cited

U.S. PATENT DOCUMENTS

| | | | |
|---|---|---|---|
| 3,280,122 | 10/1966 | Hasanyi et al. | 260/247.5 |
| 3,459,753 | 8/1969 | Boltze et al. | 424/253 |
| 4,197,300 | 4/1980 | Scagini et al. | 426/248.54 |
| 4,378,359 | 3/1983 | Chiodoni et al. | 424/253 |

FOREIGN PATENT DOCUMENTS 0011399 5/1980 European Pat. Off. .
0089028 3/1983 European Pat. Off. .

OTHER PUBLICATIONS

J. Chem. Res. (M), 1979, 0801–0809.
Arch. Exp. Path. Pharmacol., 195, 71 (1940).

*Primary Examiner*—Nicholas S. Rizzo
*Attorney, Agent, or Firm*—Karl F. Ross; Herbert Dubno

[57] ABSTRACT

Antitussive compounds of the formula I (I)

or physiologically acceptable acid addition salts thereof are disclosed, where A stands for straight or branched chain $C_{1-5}$ alkylene or $$-CH_2-CH(OH)-CH_2-,$$

$R_1$ stands for straight or branched chain $C_{1-10}$ alkyl, halogenoalkyl, hydroxyalkyl, $C_{5-6}$ cycloalkyl, vinyl, 2-ethoxyethyl, carbonylalkyl or aminoalkyl of the formula $$-(CH_2)_n-CH(R)-N(R_2)(R_3)$$

wherein R stands for hydrogen or methyl,
n is 0 to 3,
$R_2$ stands for hydrogen or straight or branched chain alkyl,
$R_3$ stands for hydrogen or straight or branched chain alkyl or,
$R_2$ and $R_3$ together with the nitrogen atom may form a 5–6 membered ring, which ring can optionally contain an oxygen or a second nitrogen atom, the latter, optionally substituted by methyl or,
$R_1$ can stand for a phenyl group of the formula $$R_4R_5C_6H_3$$

wherein
$R_4$ and $R_5$ represent independently hydrogen, chlorine, hydroxy, methoxy, ethoxy, methyl or amino or,
$R_1$ may further stand for hydroxy, in this case the compound of the formula I may exist according to the conditions in the form of tautomers of the formula Ia (Ia)

or (Ib)

and $R_1$ may further stand for benzyl, 2-diphenylethyl or theophyllin-7-yl-methyl.

6 Claims, Do Drawings

THEOPHYLLINYL-ALKYL-OXADIAZOLES, PROCESS FOR THE PREPARATION THEREOF AND PHARMACEUTICAL COMPOSITIONS CONTAINING SAME

The present invention relates to new pharmacologically active 7-substituted theophylline derivatives of the formula (I)

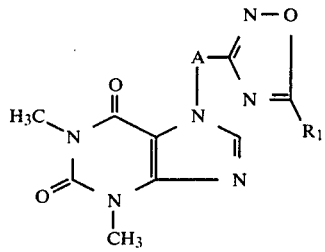

physiologically acceptable addition salts thereof and process for the preparation of the same.

In the formula I

A stands for straight or branched chained $C_{1-5}$-alkylene or

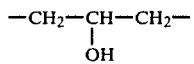

$R_1$ represents straight or branched chained $C_{1-10}$-alkyl, halogenoalkyl, hydroxyalkyl, $C_{5-6}$-cycloalkyl, vinyl, 2-ethoxy-ethyl, carbonylalkyl or aminoalkyl of the formula

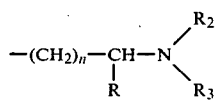

wherein

R is hydrogen or methyl n is 0, 1, 2 or 3, $R_2$ and $R_3$ stand for hydrogen, straight or branched chained alkyl containing 1 to 4 carbon atoms, or $R_2$ and $R_3$ can together with the nitrogen atom form a 5 to 6 membered ring, which can contain a second nitrogen or oxygen atom which latter ring can be substituted with methyl or $R_1$ stands for a phenyl group of the formula

wherein $R_4$ and $R_5$ represent independently a hydrogen, a chlorine atom or hydroxy, methoxy, ethoxy, methyl or amino or $R_1$ stand for hydroxy and compounds of the formula I then can be in tautomeric forms of the formula Ia

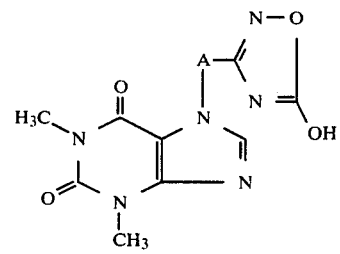

or Ib

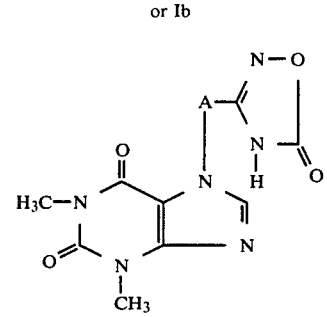

or $R_1$ is benzyl, 2,2-diphenylethyl or theophyllin-7-yl-methyl.

The present invention relates also to the salts of the compounds of the formula I—which can be, if desired, formed by acid addition by using acids selected from inorganic acids, (such as hydrogen chloride, hydrogen bromide, sulphuric acid), phosphoric acid or organic acids, (such as carboxylic acids and sulfonic acids, e.g. acetic acid, succinic acid, glycolic acid, lactic acid, tartaric acid, citric acid, ascorbic acid, maleic acid, benzoic acid, hydroxy benzoyl benzoic acid, nicotinic acid, toluene sulfonic acid), or the quaternary ammonium salts formed with alkyl halides, alkyl sulphates, and alkyl phosphates, (such as methyl iodide, methyl bromide or methyl sulphate).

The term "halogeno alkyl" as used hereinafter stands for a halogeno alkyl group containing 1 to 5 carbon atoms, such as chloromethyl, chloroethyl, chloropropyl and chlorobutyl. In the carboxyalkyl and hydroxyalkyl, preferably one alkyl groups contain 1 to 5 carbon atoms.

$R_2$ and $R_3$ preferably form together with the nitrogen atom groups selected from piperidino, piperazino, pyrrolidino, morpholino, N-methyl-piperazino.

When the compounds of the formula I contain a chiral center, both the optically active and racemic forms can be used for pharmaceutical purposes and thus the present invention includes both the optically active and racemic compounds.

The pharmaceutical utilization of codeine and codeine-like compounds for cough relief has been known for a long time. The activity of these compounds is central, i.e. they act by the depression of the coughing reflex. As this central activity is not specific, codeine and derivatives thereof have several undesirable side-effects, e.g. respiration is depressed, and therefore their use is not suggested for asthmatic patients. Recently such cough relieving agents have been discovered which do not act through the central nervous system and thus do not inhibit respiration. Certain oxadiazoles belong to this group, the most significant representative of which is Prenoxdiazin (Hungarian Pat. No. 151748.

It is known that theophylline and various derivatives thereof show a bronchodilatory and respiration improving activity and therefore these compounds play an important role in the treatment of asthma.

According to a new trend in pharmacological research attempts to have been made to combine the two favourable activities, i.e. the cough relieving and bronchodilatory activities, by using cough relieving agents which do not depress respiration. This research has so far resulted only in such pharmaceutical compositions, which combine the two various activities by mechanically combining two different types of molecules, i.e. by salt and complex formation. Such compositions are disclosed e.g. in Belgian Pat. No. 874 773 and the corresponding U.S. Pat. No. 4,197,300.

We have now found that the new theophylline derivatives according to the present invention show excellent cough relieving, antiinflammatory and bronchodilatory activity. According to the type of substitution several representatives of the group show a surprisingly stronger cough relieving activity than that of prenoxdiazin and codeine, and possess simultaneously a bronchospasmolytic and asthma inhibiting activity. From a therapeutic point of view this is extremely favorable and surprising in that the toxicity of the compounds of the formula I is only a small fraction of the toxicity of prenoxdiazin and codeine.

On the basis of the above mentioned valuable activities the compounds of the formula I can be used effective in human therapy and first of all for the treatment of the diseases of the respiratory system, of cough relieving and bronchodilatation, treatment of asthma, prevention of the same and for the treatment of inflammatory conditions.

Cough relieving activity and toxicity data of some of the compounds of the formula I and of prenoxdiazine and codeine as reference substances are shown in Table I.

TABLE 1

| A | I | $R_1$ | Cough inhibition Q % | Toxicity in mice LD$_{50}$ i.v. | mg./kg. p.o. |
|---|---|---|---|---|---|
| $CH_2$ |  | $CH_3$ | 54.31 | 416 | 1430 |
| $CH_2$ | $(CH_2)_2$ | $CH_3$ | 51.15 | 390 | 1400 |
| $CH_2$ | $(CH_2)_2$ | $N(C_2H_5)_2$ | 56.66 | 215 | 1405 |
| $CH_2$ | $(CH_2)_2$ | —N⟩ (piperidine) | 54.15 | 240 | 1550 |
| $CH_2$ | $(CH_2)_2$ | —N⟩O (morpholine) | 55.40 | 230 | 1530 |
| $CH_2$ | $(CH_2)_2$ | —N⟩NCH$_3$ (N-methylpiperazine) | 54.50 | 224 | 1670 |
| $(CH_2)_2$ | $(CH_2)_2$ | —N⟩O (morpholine) | 48.56 | 217 | 2600 |
| $(CH_2)_2$ | $(CH_2)_2$ | NHi.Pr | 54.66 | 200 | 1750 |
| $(CH_2)_3$ | $(CH_2)_2$ | $N(C_2H_5)_2$ | 51.48 | 237 | 2250 |
| $(CH_2)_3$ | $(CH_2)_2$ | —N⟩O (morpholine) | 47.66 | 220 | 1900 |
| $CH_2CH(OH)CH_2$ | $(CH_2)_2$ | —N⟩NCH$_3$ (N-methylpiperazine) | 48.60 | 215 | 1800 |
| Prenoxdiazine (comparative) |  |  | 44.50 | 34 | 920 |
| Codeine (comparative) |  |  | 50.00 | 54 | — |

Q = Cough relieving induced by 15% citric acid spray in guinea pigs one hour after administration of the substances (50 mg/kg, i.m.) expressed in % related to the control.

The table I shows that the absolute activity of the compounds of the formula I is in most cases better than that of the referential substances, but the therapeutic index thereof is far more favorable. The table also shows that neither the chain length A nor the substituent $R_1$ influences the cough relieving activity and the toxicity since by changing same said activity and toxicity do not change significantly. The greatest part of the compounds according to the invention can be utilized in therapy with success. The ratio of i.v. and p.o. toxicity show that the resorption of the compounds of the formula I from the digesting system is rather good. This is proved by the cough relieving dosage curves obtained by intraduodenal and per os administration.

It must be emphasized that as opposed to prenoxdiazine most part of the compounds of the formula I are water soluble.

A special group of the compounds of the formula I are those compounds in which $R_1$ stands for alkyl, aralkyl, or aryl. These compounds possess a valuable, long-lasting cough relieving, antiasthmatic, bronchodilatory and antiinflammatory activity. Thus for example 7-[(5-methyl-1,2,4-oxadiazol-3-yl)-methyl]-theophylline apart from the cough relieving activity indicated in Table I, decreases the bronchial spasm induced by histamine both in in vitro tests measured on a trachea stria isolated from rabbit and in vivo tests measured in guinea pig according to Konzett and Rossler [Arch. exp. Path. Pharmacol. 195, 71 (1940)], the duration of activity is considerably longer than in case of theophylline ethylene diamine and it also prevents the spasm caused by acetyl choline or serotonine. This activity is significant in relieving cough of the asthmatic type.

The above mentioned compounds therapeutic index is on the basis of cough relieving activity, or i.v. toxicity measured in mice and rats about five times more favorable than that of the reference compound codeine and more than ten times more favorable than that of prenoxdiazin. The compound increases the respiration volume and simultaneously reduces the respiration number according to tests carried out in narcotized cats, this activity being favorable for the treatment of diseases of the respiration system. A significant therapeutic activity of this group is the prevention of the chronic asthma caused by polluted air, polluted mainly with tobacco smoke. This activity is proved by a long-lasting test performed on rats.

Another special group of the compounds according to the invention are the compounds having an alkyl amino group in place of $R_1$. These compounds also possess valuable cough relieving, bronchodilatory and particularly antiinflammatory properties. 7-[(5-(2-diethylamino-ethan-1-yl)-1,2,4-oxadiazol-3-yl)-methyl]-theophylline shows apart from the cough relieving and bronchodilatory activity a strong (comparable with indomethacin) anti-inflammatory activity tested by i.m. administration in rat paw carrageenin oedema test. This activity is important in cough relieving accompanied by inflammation in the respiration system.

The compounds of the formula I can be prepared according to the invention as follows:

(a) reacting an amidoxime of the formula II

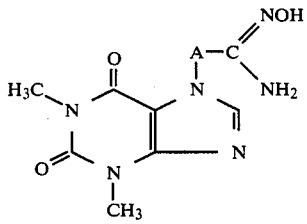 /II/ wherein A is as given above—with an acid of the formula III

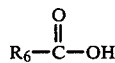 /III/ wherein $R_6$ is identical with $R_1$ or is a group suitable for converting $R_6$ into $R_1$, preferably vinyl, 2-ethoxyethyl, $C_{3-4}$ oxoalkyl, halogenalkyl, O-toxyl alkyl or O-mesyl alkyl and/or with derivatives thereof suitable for acylation in order to produce compounds of the formula Ic

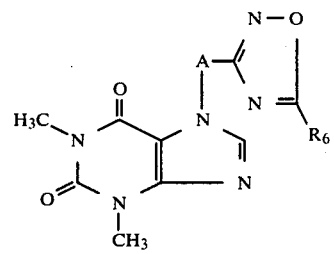 /Ic/ and converting, if desired $R_6$ to $R_1$ or (b) reacting an amidoxime of the formula II

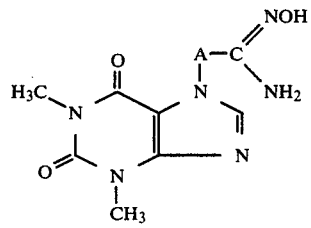

with an acid of the formula III

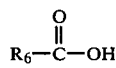 /III/ or a derivative thereof suitable for acylation in order to produce an acylated derivative of the compound of the formula II, i.e. a compound of the formula IV

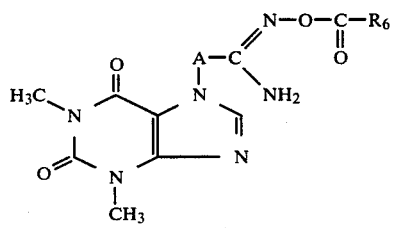 /IV/ wherein A and $R_6$ are as defined above—followed by the isolation of the compound of the formula IV or without isolation thereof forming a ring under elimination of water and if desired converting group $R_6$ to $R_1$ or (c) reacting a compound of the formula V

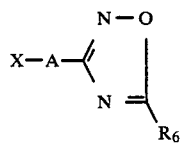

wherein A is as defined above, X stands for halogen or sulfonic acid ester—with theophylline in the presence of an organic solvent and/or diluent, preferably dimethylformamide or alcohol, preferably ethanol, isopropylalcohol, or an inorganic base, preferably alkali hydroxide, particularly potassium hydroxide, or sodium hydroxide, alkali carbonate, preferably sodium carbonate or potassium carbonate or organic base, preferably pyridine, or piperidine or with an alkali salt of theophylline, preferably theophylline sodium, theophylline potassium in a solution or suspension, preferably in isopropyl alcohol under heating and converting, if desired, an $R_6$ group into $R_1$ group or (d) in order to produce a special group of the compounds of the formula I, i.e. the compounds of the formula Id

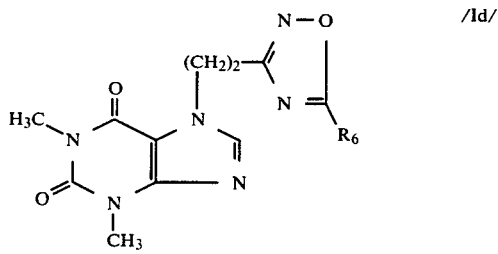

wherein $R_6$ is as defined above—reacting an olephine of the formula VI

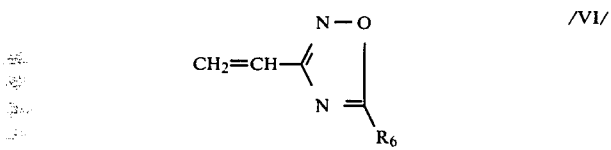

wherein $R_6$ is as given above—with theophylline in the presence of a basic catalyst, preferably a quaternary ammonium hydroxide, particularly Triton-B, under heating and converting, if desired a group $R_6$ into $R_1$, or (e) in order to produce compounds of the formula I containing a group of the formula

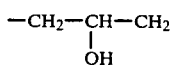

in place of A, reacting an epoxide of the formula VII

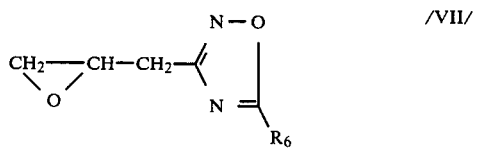

wherein $R_6$ is as defined above—with theophylline, preferably in the presence of a basic catalyst, preferably pyridine, in an organic solvent, preferably ethanol, and converting, if desired, $R_6$ to $R_1$.

Process variant (a) is preferably conducted by reacting an amidoxime of the formula II with an ester of the formula $R_6COOR_7$ wherein $R_6$ is as defined above and $R_7$ is alkyl, preferably methyl or ethyl, in the presence of a base, preferably alkali or alkali earth metal hydroxide, particularly potassium hydroxide, sodium hydroxide or alkali alkoxide, preferably sodium ethylate or sodium methylate and in a polar or apolar organic solvent and/or diluting agent under heating, preferably at 50°–150° C., most preferably at the boiling point of the solvent and/or diluting agent. In case of solvents of lower boiling point, e.g. methanol the reaction may be performed preferably under pressure, making possible thereby the use of a temperature being higher than the boiling point of the solvent. As an advantageous embodiment of the process according to the invention as polar solvents $C_{1-4}$ alcohols, N-alkyl-acid amides such as dimethylformamide, apolar solvents, such as aromatic hydrocarbons, such as benzene, chlorobenzene, toluene, xylene are preferred, by means of which the leaving water and the alcohol may be subjected to azeotrop distillation.

The reaction in process variant (a) may also be performed by reacting an amidoxime of the formula II with a carboxylic acid of the formula III and/or acid anhydride under heating in the presence of an organic solvent. As solvents aromatic hydrocarbons may be used and it is particularly preferred if the solvent is the acylating acid and/or acid anhydride itself. The acylation and the ring closure are preferably conducted at 50°–150° C., preferably at 90°–110° C.

The reaction time for process variant (a) depends on the quality of the used reactant and the solvent as well as on the reaction temperature and pressure and it may vary between 0.5 and 24 hours.

The reaction according to process variant (b) can preferably be performed by conducting the acylation preferably with an acid anhydride of the formula $(R_6CO)_2O$ or an acid derivative of the formula $R_6COX$——wherein X stands for halogen—particularly with acid chlorides in the presence of an organic solvent and/or diluting agent, preferably acetone, pyridine, benzene, toluene, dimethylformamide, or in case of acylation with acid anhydride the reaction is performed in the presence of excess anhydride, dialkyl ether containing $C_{2-4}$ alkyl groups, phenyl alkyl ether, dioxan, chlorinated hydrocarbons containing 1 to 4 carbon atoms, preferably dichloromethane, chloroform, or a suitable acid. In case of acylation with acid halides the reaction is preferably conducted in the presence of an inorganic or organic base as acid binding agent. As inorganic acid binding agents, alkali and alkali earth metal carbonates, such as sodium carbonate, potassium carbonate, calcium carbonate, or alkali hydrogen carbonates, such as sodium hydrogen carbonate and as organic acid binding agents tertiary amines, such as pyridine or triethylamine are preferred but also the starting amidoxime or if $R_6$ is basic, then the formed acyl derivative of the formula IV can serve as acid binding agent.

The ring closure of the oxadiazole ring in process variant (b) can be carried out in a polar solvent, preferably in organic acids, acid anhydride, pyridine, dimethylformamide, or an apolar solvent and/or diluting agent, preferably in aromatic solvents, such as toluene under heating, or without any solvent by pyrolysis. The process variant is performed preferably by conducting the ring closure of the compound of the formula IV in an aqueous, organic solvent medium or in an aqueous-organic solvent medium at a pH value being between 6 to 8 under heating or without heating. As organic solvents water soluble compounds, such as acetone, dioxan, $C_{1-3}$ alcohols may be used. Ring closure may be conducted according to the solubility conditions of the compound of the formula IV and the quality of $R_6$ at a temperature ranging from 20° to 100° C. In case of water soluble compounds of the formula IV the condensation is preferably performed in an aqueous solution at 80° to 100° C., at a pH of 6.6–7.4. In order to ensure an optimal pH for the ring-closure the presence of a weak base in a catalytic amount is preferred, and for this purpose one may use a salt formed with a strong base and a carboxylic acid corresponding to $R_6$, such as sodium, or potassium salt, or sodium carbonate, potassium carbonate or tertiary amines, such as triethyl amine may be used.

Starting materials for processes (a) and (b), i.e. theophyllinyl-alkyl carboxamidoximes of the formula II can be prepared by methods known per se, preferably by reacting preferably the suitable theophyllinyl alkyl nitriles and hydroxylamine by heating the reactants for several hours in methanol or ethanol.

Oxadiazoles of the formula V serving as starting materials in process variant (c) can be prepared by methods known per se, preferably by reacting the corresponding 3-(ω-hydroxyalkyl)-5-substituted-1,2,4-oxadiazoles with thionyl halides, preferably thionyl chloride or tosyl chloride or mesyl chloride (J. Chem. Research {M}, 1979, 801).

Olefins of the formula VI serving as starting material for the process variant (d) can be prepared by methods known per se (J. Chem. Research {M} 1979, 801).

Epoxides of the formula VII serving as starting material for the process variant (e) can be prepared from the corresponding 3-(2,3-dihydroxy-propyl)-5-substituted-1,2,4-oxadiazoles by eliminating water by methods known per se.

Compounds of the formula Ic according to the invention and O-acyl-amidoximes of the general formula IV, wherein $R_6$ stands for vinyl, can be prepared by reacting amidoximes of the formula II and the corresponding acrylic acid derivatives, preferably acrylic acid chloride by methods given for processes (a) and (b), preferably in the presence of sodium carbonate in acetone.

Compounds of the formula Ic, wherein $R_6$ stands for 2-ethoxy-ethyl group, can be prepared from amidoximes of the formula II with ethyl acrylate in the presence of sodium ethylate in methanol medium under heating.

The compounds of the general formula Ic and IV, wherein $R_6$ is halogeno alkyl, can be prepared by reacting the corresponding halogeno-alkane carboxylic acid chloride with amidoximes of the general formula II, preferably in acetone in the presence of alkali carbonate by acylation under cooling, if desired by ring closure. The ring closure of the compounds of the general formula IV can be performed in these cases preferably in a toluene solution and/or in suspension or by pyrolysis, preferably by using reduced pressure.

Compounds of the general formula Ic and O-acylamidoximes of the formula IV, wherein $R_6$ stands for vinyl, 2-ethoxy-ethyl, halogenalkyl containing 1 to 4 carbon atoms, O-mesyl-alkyl, O-tosyl-alkyl, can be reacted with amines of the general formula $HNR_2R_3$ resulting compounds of the general formula I wherein $R_1$ stands for $(CH_2)_2NR_2R_3$ or $(CH_2)_nNR_2R_3$.

Amination can be conducted with a 5–100% excess of amine in an organic solvent, preferably toluene at 50° to 150° C. under heating. It is preferred to carry out the acylation, amination, and ring closure without isolating the intermediate product in one step.

Oxadiazoles of the general formula Ic wherein $R_6$ stands for oxoalkyl, can be obtained from amidoximes of the general formula II by acylation and ring closure of the corresponding oxo-alkane-carboxylic acid derivatives. Oxo alkyl group is subjected to reductive condensation with amines of the formula $R_8NH_2$— wherein $R_8$ stands for $R_2$ except hydrogen—and thus the corresponding compounds of the formula I containing a secondary amino alkyl group can be obtained. As upon catalytic hydrogenation the 1,2,4-oxadiazole ring is opened, the reductive condensation is carried out preferably in an organic solvent followed by a reduction of the azomethine bond with sodium tetrahydroborate.

Oxadiazoles of the formula Ic wherein $R_6$ stands for $(CH_2)_n$—$NH_2$— wherein n stands for 1–4—can be alkylated with alkyl halides, alkyl sulphates or alkyl phosphates and thus compounds of the formula I are obtained, wherein $R_1$ stands for $(CH_2)_nN(R_2)_2$ or $—(CH_2)_n—N^+(R_2)_3Q^-$, wherein $Q^-$ represents an anion corresponding to the alkylating agent. Methylation of the primary amino group can be preferably performed by methods known per se using formaldehyde in formic acid.

The new compounds of the formula I according to the invention can be utilized in pharmaceutical compositions containing an effective amount of the active ingredient together with pharmaceutically acceptable organic or inorganic solid or liquid carriers. The pharmaceutical compositions may be administered enterally or parenterally. Advantageous dosage units are syrups, tablets, capsules, suppositories, containing the active ingredient admixed with diluent, such as lactose, dextrose, sucrose, mannitol, sorbitol, cellulose, and derivatives thereof, glycerol and/or lubricants, such as silica, talc, stearic acid, and salts thereof, polyethylene glycol, binding agents, such as silicates, starch, and derivatives thereof, gelatine, methyl cellulose, filling agents, foaming agents, dyes, flavoring agents. The pharmacologically active new compounds may be prepared in the form of parenterally administrable compositions, such as injectable solutions, or infusion solutions. These pharmaceutical compositions, which can optionally contain other pharmacologically active ingredients, can be prepared by methods known per se, e.g. by blending, granulation, methods for preparing dragées, dissolution, lyophilization and they contain about 0.2–100%, preferably 1–50% active ingredient. The dosage depends on various factors, such as route of administration, age, and/or condition of the patient etc. The oral dosage is about 0.1–2.0 g per day in case of persons of 70 kg body weight. The further details of the invention can be found in the following Examples which serve merely for illustration and for limitation.

A. PREPARATION EXAMPLES

Example 1 a. 25.2 g. of 2-(theophyllin-7-yl)-acetamidoxime are heated in 250 cm³ acetic anhydride until dissolution, the solution is allowed to stand at room temperature overnight. Upon trituration with 250 cm³ diethyl ether 27.6 g. (94% yield) 2-(theophyllin-7-yl)-O-acetylacetamidoxime are obtained. M.p.: 201° C. (ethanol).

b. To 25.2 g. 2-(theophyllin-7-yl)-acetamidoxime in a mixture of 400 cm³ abs. acetone and 10.2 g. of triethylamine 78.5 g. acetyl chloride are added under stirring. 23.1 g (78% yield) of 2-(theophyllin-7-yl)-O-acetyl-acetamidoxime are obtained. M.p.: 201° C.

c. 2.94 g. of 2-(theophyllin-7-yl)-O-acetyl-acetamidoxime are heated on water bath for 2 hours in 20 cm³ of pyridine and the solvent is distilled off at reduced pressure. The residue is crystallized from water and thus 2.58 g. (93% yield) of 7-[(5-methyl-1,2,4-oxadiazol-3-yl(-methyl]-theophylline are obtained. M.p.: 135°–136° C. Ring closure may be carried out with acetic anhydride, acetic acid or acetic anhydride-acetic acid mixture instead of pyridine.

d. 15.12 g of 2-(theophyllin-7-yl)-acetamidoxime are heated on water bath for two hours with a mixture of 120 cm³ acetic acid and 8 cm³ of acetic anhydride. The solvent is distilled off and 16.06 g. (91%) of 7-[(5-methyl-1,2,4-oxadiazol-3-yl)-methyl]-theophylline are obtained. M.p.: 135° C. (methanol).

e. 5.04 g. 2-(theophyllin-7-yl)-acetamidoxime, 2.16 g. of sodium methylate, 10 cm³ ethyl acetate and 200 cm³ of toluene are heated under stirring by using a water condenser for 20 hours and further 10 cm³ ethyl acetate are added to the mixture in five portions. The solvent is distilled off. After crystallization from water 4.1 g. (74% yield) 7-[(5-methyl-1,2,4-oxadiazol-3-yl)-methyl]-theophylline are obtained. M.p.: 135°–136° C.

f. 5.04 g. of 2-(theophyllin-7-yl)-acetamidoxime, 2.16 g. of sodium methylate and 10 cm³ ethyl acetate are heated under shaking and under pressure in 150 cm³ methanol at 100° C. for 8.5 hours. After processing 4.8 g. (87% yield) of 7-[(5-methyl-1,2,4-oxadiazol-3-yl)-methyl]-theophylline are obtained. M.p.: 135°–136° C.

g. 20.2 g. of theophylline-sodium, 300 cm³ isopropyl alcohol and 13.2 g. of 3-chloromethyl-5-methyl-1,2,4-oxadiazole are heated under stirring for 10 hours. After processing 20.5 g. (74.2% yield) of 7-(5-methyl-1,2,4-oxadiazol-3-yl)-methyl-theophylline are obtained. M.p.: 134°–135° C.

h. 2.94 g. 2-(theophyllin-7-yl)-O-acetyl-acetamidoxime are heated with 20 cm³ acetic acid for 2 hours. 2.62 g. (94% yield) of 7-[(5-methyl-1,2,4-oxadiazol-3-yl)-methyl]-theophylline are obtained. M.p.: 134°–135° C.

i. 29.42 g. of 2-(theophyllin-7-yl)-O-acetyl-acetamidoxime are heated in 400 cm³ of water of 97°–99° C. until dissolution whereafter the pH is adjusted to 7 with triethylamine. Heating is continued for 5.5 hours and the solution is cooled and pH is adjusted to 1 with hydrochloric acid, and the solution is extracted with 4×50 cm³ dichloroethane. The solvent is distilled off and the residue is recrystallized from water. 24.5 g. of 7-[(5-methyl-1,2,4-oxadiazol-3-yl)-methyl]-theophylline are obtained. M.p.: 135°–136° C.

j. The amidoxime used in the previous Examples is prepared as follows: 10.96 g. of 7-cyano-methyl-theophylline, 7.64 g. of hydroxylamine hydrochloride, 5.98 g. of sodium methylate and 50 cm³ of methanol are heated on water bath for 5 hours. 9.85 g. (78% yield) 2-(theophyllin-7-yl)-acetamidoxime are obtained. M.p.: 224° C. (from aqueous ethanol).

k. O-acetyl-amidoxime is prepared as follows: 25.42 g. 2-(theophyllin-7-yl)-acetamidoxime, 100 cm³ dichloroethane and 10.8 g. of acetic anhydride are stirred at 50°–55° C. for 3 hours. 28.8 g. 2-(theophyllin-7-yl)-O-acetyl-acetamidoxime are obtained which is directly suitable for further use. M.p.: 197°–198° C., Example 2

25.2 g. of 2-(theophyllin-7-yl)-acetamidoxime are acylated in 400 cm³ anhydrous acetone with 8.6 g. of sodium hydrogen carbonate and a solution of 11.3 g. chloroacetyl chloride in 40 cm³ acetone. 27.2 g. (83% yield) of 2-(theophyllin-7-yl)-O-chloroacetyl-acetamidoxime are obtained. This product is heated to constant weight at 105° C. in vacuo (at 133 Pa pressure) for about 20 to 60 minutes. The product is then recrystallized from methanol. 19.1 g (62% yield) of 7-[(5-chloromethyl-1,2,4-oxadiazol-3-yl)-methyl]-theophylline are obtained. M.p.: 146°–148° C.

Example 3 a. 5.04 g. 2-(theophyllin-7-yl)-acetamidoxime, 2.16 g. of sodium methylate, 6.37 g. of diethyl aminoacetic acid ethylester and 100 cm³ of toluene are heated for 15 hours and the hot mixture is filtered, evaporated. The residue is recrystallized from cyclohexane. 5.4 g. of 7-[(5-diethylaminomethyl-1,2,4-oxadiazol-3-yl)-methyl]-theophylline are obtained (82% yield). M.p.: 68°–70° C. Hydrochloride salt melts at 206°–210° C.

b. 9.0 g. of 7-[(5-chloromethyl-1,2,4-oxadiazol-3-yl)-methyl]-theophylline, 6 cm³ diethylamine and 50 cm³ toluene are heated on water bath for 8 hours under stirring. The mixture is evaporated at reduced pressure and the residue is washed with water, dissolved in 50 cm³ hot ethanol, treated with activated charcoal and treated with ethanol in hydrochloric acid. 8.3 g of 7-[(5-diethylaminomethyl-1,2,4-oxadiazol-3-yl)-methyl]-theophylline-hydrochloride salt are obtained. M.p.: 207°–210° C.

c. 5.04 g. of 2-(theophyllin-7-yl)-acetamidoxime are dissolved in 40 cm³ anhydrous pyridine and to the solution 3.0 g. of diethyl amino acetyl chloride are added dropwise under stirring and cooling at max. 20° C. whereafter the mixture is stirred on water bath for 2 hours. The mixture is evaporated to dryness and hydrochloric acid salt is formed in ethanol, 6.1 g. (83.8% yield) of 7-[(5-diethylamino-methyl-1,2,4-oxadiazol-3-yl)-methyl]-theophylline-hydrochloride are obtained (m.p.: 208°–210° C.).

d. To a suspension of 3.27 g. of 2-(theophyllin-7-yl)-O-chloroacetyl-acetamidoxime in 20 cm³ of toluene prepared according to Example 2, 3 cm³ diethylamine are added dropwise, the mixture is heated for 8 hours. Hydrochloride salt is formed in ethanol and 2.6 g. (71% yield) of 7-[(5-diethylaminomethyl-1,2,4-oxadiazol-3-yl)-methyl]-theophylline-hydrochloride are obtained (m.p.: 207°–209° C.).

e. 5.04 g. of 2-(theophyllin-7-yl)-acetamidoxime, 2.16 g. of sodium methylate, 6.37 g. of diethylamino acetic acid ethylester and 80 cm³ methanol are stirred for 10 hours at 100° C. in a closed system under pressure. 5.2 g. (80% yield) of 7-[(5-diethylaminomethyl-1,2,4-oxadiazol-3-yl)-methyl]-theophylline are obtained. m.p.: 69°–70° C. (cyclohexane).

f. 30.9 g. 7-[(5-chloromethyl-1,2,4-oxadiazol-3-yl)-methyl]-theophylline are heated in 300 cm³ dimethylformamide with 18.5 g. potassium phthalamide under stirring for 6 hours. Dimethylformamide is distilled off at reduced pressure, and the residue is triturated with 300 cm³ ethanol and 5.2 g. of hydrazine hydrate are added, the mixture is heated on water bath for 2 hours, acidified with concentrated aqueous hydrochloric acid, the mixture is boiled and filtered when hot and the filtrate is evaporated. After crystallization from methanol 24.7 g. (74.2% yield) of 7-[(5-aminomethyl-1,2,4-oxadiazol-3-yl)-methyl]-theophylline-hydrochloride are obtained, m.p.: 204°–207° C.

g. 3.34 g. of 7-[(5-aminomethyl-1,2,4-oxadiazol-3-yl)-methyl]-theophylline-hydrochloride, 0.8 g. of sodium formiate and 30 cm$^9$ 90% formic acid are heated on water bath until dissolution and after cooling 4.5 cm$^3$ of 30% formic acid solution is added. The mixture is heated on water bath for 8 hours, evaporated to dryness. The residue is triturated with 10 cm$^3$ 10% sodium hydroxide solution, the organic layer is extracted with chloroform. Hydrochloride salt is formed in ethanol. 1.95 g. (55% yield) of 7-[(5-dimethylaminomethyl-1,2,4-oxadiazol-3-yl)-methyl]-theophylline-hydrochloride are obtained. M.p.: 211°–213° C.

h. 3.34 g. of 7-[(5-aminomethyl-1,2,4-oxadiazol-3-yl)-methyl]-theophylline-hydrochloride, 4.5 g. of potassium carbonate are stirred in 80 cm$^3$ dimethylformamide with 2.2 g. of ethyl bromide for 7 hours. The solvent is distilled off at reduced pressure and hydrochloric acid in ethanol is used for salt formation. Thus 2.2 g. (62% yield) of 7-[(5-diethylamino-methyl-1,2,4-oxadiazol-3-yl)-methyl]-theophylline-hydrochloride are obtained. M.p.: 207°–208° C. (ethanol).

Example 4 a. 25.2 g. of 2-(theophyllin-7-yl)-acetamidoxime, 200 cm$^3$ toluene, 6.8 g. of sodium ethylate, 34.6 g. of β-diethylamino-propionic acid ethyl ester are heated in a flask equipped with a water condenser under stirring for 4 hours, the solution is filtered. Salt is formed with 11.6 g. of maleic acid. 40.5 g. (85% yield) of 7-[{5-(2-diethylamino-ethan-1-yl)-1,2,4-oxadiazol-3-yl}-methyl]-theophylline-maleinate are obtained. M.p.: 127°–128° C.

b. 5.04 g. of 2-(theophyllin-7-yl)-acetamidoxime, 2.16 g. of sodium methylate, 6.4 g. of diethylamino propionic acid ethyl ester and 100 cm$^3$ of toluene are reacted according to Example a. 6.3 g. (87% yield) of 7-[{5-(2-diethylamino-ethan-1-yl)-1,2,4-oxadiazol-3-yl}-methyl]-theophylline are obtained. M.p.: 69°–70° C. (cyclohexane).

c. 25.2 g. of 2-(theophyllin-7-yl)-acetamidoxime, 400 cm$^3$ of acetone, and 8.6 g. of sodium hydrogen carbonate are admixed and to this mixture a solution of 9.1 g. acrylic acid chloride in 40 cm$^3$ of acetone is added. 28.1 g. of 2-(theophyllin-7-yl)-O-acroyl/-acetamidoxime are obtained. M.p.: 160°–165° C. (methanol).

d. 6.12 g. of raw 2-(theophyllin-7-yl)-O-acroylacetamidoxime are heated with 25 cm$^3$ diethylamine under reflux on a 110° C. water bath for 6 hours. The basis is distilled off at reduced pressure, the residue is crystallized from cyclohexane. 5.8 g. (80% yield) of 7-[[5-(2-diethylamino-ethan-1-yl)-1,2,4-oxadiazol-3-yl]-methyl]-theophylline are obtained. M.p.: 78°–80° C.

e. A mixture of 12.6 g. of 2-(theophyllin-7-yl)-acetamidoxime, 10 g. of ethyl acrylate, 5.2 cm$^3$ of diethylamine, 3.4 g. of sodium ethylate and 200 cm$^3$ of ethanol is heated for 15 hours under stirring under pressure at 100° C. 5.8 g. of maleic acid salt is formed. 14.5 g. (61% yield) of 7-[[5-(2-diethylamino-ethan-1-yl)-1,2,4-oxadiazol-3-yl]-methyl]-theophylline-maleinate are obtained. M.p.: 126°–128° C.

f. 12.6 g. 2-(theophyllin-7-yl)-acetamidoxime, 10 g. of ethyl acrylate, 220 cm$^3$ of ethanol and 3.4 g. of sodium ethylate are heated under stirring for 15 hours. 16 g. (95% yield) of raw 7-[[5-(2-ethoxy-ethyl)-1,2,4-oxadiazol-3-yl]-methyl]-theophylline are obtained. This product is heated with 20 cm$^3$ diethylamine under stirring for 8 hours on a 110° C. oil bath. The mixture is then evaporated at reduced pressure, washed by trituration with water and salt is formed with 5.8 g. of maleic acid in hot ethanol. 16.2 g. (68% yield) of 7-[{5-(2-diethylamino-ethan-1-yl)-1,2,4-oxadiazol-3-yl}-methyl]-theophilline-maleinate are obtained. M.p.: 125°–128° C.

g. 5.04 g. of 2-(theophyllin-7-yl)-acetamidoxime, 4.8 g. hydracrylyc acid ethyl ester, 2.16 g. of sodium ethylate and 100 cm$^3$ of methanol are heated under pressure at 100° C. for 12 hours. The solvent is distilled off and the residue is crystallized from water. 5.3 g. (87% yield) of 7-[{5-(2-hydroxy-ethyl)-1,2,4-oxadiazol-3-yl}-methyl]-theophylline are obtained, m.p.: 145° C. The raw hydroxy ethyl compound is heated with 20 cm$^3$ thionyl chloride and 20 cm$^3$ benzene for 2 hours. The solvent is distilled off and the obtained 7-[{5-(2-chloroethyl)-1,2,4-oxadiazol-3-yl}-methyl]-theophylline is stirred in 50 cm$^3$ of dimethylformamide with 6 cm$^3$ diethylamine and 5 g. of potassium carbonate vigorously for 10 hours at 100° C. 4.4 g. (61% yield) of 7-[{5-(2-diethylaminoethyl)-1,2,4-oxadiazol-3-yl}-methyl]-theophylline are obtained. M.p.: 65°–68° C. (cyclohexane).

Example 5

5.04 g. of 2-(theophyllin-7-yl)-acetamidoxime, 5.76 g. of levulinic acid ethylester, 1.12 g. of potassium hydroxide and 100 cm$^3$ of toluene are boiled in a flask equipped with water condenser for 1.8 hours, toluene is evaporated. 5.3 g. (83% yield) of 7-[{5-butan-(3-on-1-yl)-1,2,4-oxadiazol-3-yl}-methyl]-theophylline are obtained. M.p.: 135°–140° C. (ethanol).

Example 6

3.32 g. of 7-[{5-(butan-3-on-1-yl)-1,2,4-oxadiazol-3-yl}-methyl]-theophylline prepared according to the previous Example are heated in 80 cm$^3$ benzene with 6 cm$^3$ isopropylamine under pressure at 80° C. for 4 hours. The mixture is evaporated and the residue is dissolved in 80 cm$^3$ methanol and reduced with 0.8 g. of sodium tetrahydroborate. 2.0 g. (53% yield) of 7-[{5-(3-isopropylamino-butan-1-yl)-1,2,4-oxadiazol-3-yl}-methyl]-theophylline are obtained. M.p.: 55°–61° C.

Example 7

25.2 g. of 2-(theophyllin-7-yl)-acetamidoxime, 200 cm$^3$ toluene and 6.8 g. of sodium ethylate and 37.4 g. of γ-diethylamino-butyric acid ethyl ester are reacted according to Example 4a and thus 38 g. (77% yield) of 7-[{5-(3-diethylamino-propan-1-yl)-1,2,4-oxadiazol-3-yl}-methyl]-theophylline maleinate are obtained. Melting point: 119°–121° C.

Example 8

25.2 g. of 2-(theophyllin-7-yl)-acetamidoxime, 200 cm$^3$ toluene, 6.8 g. of sodium ethylate and 40.2 g. of δ-diethylamino valerianic acid ethyl ester are reacted according to Example 4a and 40.9 g. (81% yield) of 7-[{5-(4-diethylaminobutan-yl)-1,2,4-oxadiazol-3-yl}-methyl]-theophyllinemaleinate are obtained, m.p.: 130°–132° C.

Example 9 a. 13.3 g. of β-(theophyllin-7-yl)-propionic acid amidoxime are dissolved in 40 cm³ of acetic anhydride and the solution is heated for 1 hour. 5.1 g. (88% yield) of 7-[2-(5-methyl-1,2,4-oxadiazol-3-yl)-ethan-1-yl]-theophylline are obtained, m.p.: 115°–116° C. (ethylacetate).

b. 2.6 g. of β-(theophyllin-7-yl)-propionic acid amidoxime, 0.68 g. of sodium ethylate, 10 cm³ of ethyl acetate and 30 cm³ of ethanol are heated at 110° C. under pressure for 12 hours. Thus 2.2 g. (76% yield) of 7-[2-(5-methyl-1,2,4-oxadiazol-3-yl)-ethan-1-yl]-theophylline are obtained. M.p.: 113°–115° C. (ethanol).

c. 2.2 g. of 3-vinyl-5-methyl-1,2,4-oxadiazole, 30 cm³ dimethylformamide and 0.2 cm³ Triton-B catalyst are boiled with 3.6 g. of theophylline for 1 hour. The solvent is distilled off and the residue is crystallized from ethanol. 4.2 g. (72% yield) of 7-[2-(5-methyl-1,2,4-oxadiazol-3-yl)-ethan-1-yl]-theophylline are obtained. m.p.: 112°–114° C.

d. 2.92 g. of 3-(2-chloroethyl)-5-methyl-1,2,4-oxadiazole, 50 cm³ isopropylalcohol and 4.0 g. of theophylline sodium are heated for 8 hours. 5.3 g. (91% yield) 7-[2-(5-methyl-1,2,4-oxadiazol-3-yl)-ethan-1-yl]-theophylline are obtained, m.p.: 113°–114° C. (water).

Example 10 a. 39.19 g. of metal sodium are dissolved in 500 cm³ of methanol and the solution is added to a solution of 118.4 g. of hydroxylamine hydrochloride in 1000 cm³ hot methanol. The solution is filtered and the filtrate is added to 112.6 g. of 7-(2-hydroxy-3-cyanopropan-1-yl)-theophylline (prepared as disclosed in DE-PS No. 1 064 066) and the mixture is heated for 30 hours. 125.0 g. (93% yield) 3-(theophyllin-7-yl)-2-hydroxy propionic acid amidoxime hydrate are obtained. M.p.: 200°–202° C. (Empirical formula: C₁₁H₁₈N₆O₅).

b. 6.28 g. amidoxime prepared according to the previous Example, 1.38 g. of sodium ethylate, 30 cm³ ethyl acetate and 100 cm³ of ethanol are boiled under stirring for 12 hours. 5.7 g. (89% yield) of 7-[2-hydroxy-3-(5-methyl-1,2,4-oxadiazol-3-yl)-propan-1-yl]-theophylline are obtained, m.p.: 148°–150° C. /ethanol/.

c. 1.4 g. 3-(2,3-epoxy-propyl)-5-methyl-1,2,4-oxadiazole and 1.8 g. of theophylline are boiled under stirring in a mixture of 20 cm³ isopropyl alcohol and 0.1 cm³ of pyridine for 8 hours. 2.75 g. (86% yield) of 7-[2-hydroxy-3-(5-methyl-1,2,4-oxadiazol-3-yl)-propan-1-yl]-theophylline are obtained.

Example 11

12.56 g. of amidoxime prepared according to the a/part of the previous Example, 14.80 g. of β-piperidinopropionic acid ethyl ether, 2.16 g. of sodium methylate and 200 cm³ of toluene are boiled for 5 hours, the mixture is evaporated and the residue is treated with an 1:1 mixture of benzene and ether. 11.7 g. (71% yield) of 7-[2-hydroxy-3-{5-(2-piperidino-ethan-1-yl)-1,2,4-oxadiazol-3-yl}-propan-1-yl]-theophylline are obtained, m.p.: 110°–111° C. The maleinate melts at 179°–180° C.

Example 12 a. 57.9 g. of 7-(3-chloro-propan-1-yl)-theophylline, 12.29 g. of sodium cyanide, 2.0 g. of sodium iodide and 400 cm³ of dimethylformamide are stirred at 90° C. for 3 hours. 49.1 g. (88% yield) of γ-(theophylline-7-yl)-butyronitrile are obtained. M.p.: 146°–150° C.

b. One may proceed as disclosed in Example 1j (and from the nitrile according to Example 12a) γ-(theophylline-7-yl)-butyric acid amidoxime is precipitated by reaction with hydroxylamine. The product becomes colored at 190° C. Yield: 94%.

c. 7.29 g. of γ-(theophylline-7-yl)-butyric acid amidoxime, 9.01 g. of β-diethylamino-propionic acid ethyl ester, 1.4 g. of sodium methylate and 80 cm³ of toluene are heated for 2 hours. The product is reacted with maleic acid and 10.45 g. (80% yield) of 7-[3-5-(2-diethylamino-ethan-1-yl)-1,2,4-oxadiazol-3-yl-propan-1-yl]-theophylline-maleinate are obtained, m.p.: 134°–136° C.

Example 13 a. 3.85 g. of 2-(4-chloro-butan-1-yl-oxy)pyrane, 4.04 g. of theophylline sodium, 0.01 g. of sodium iodide and 15 cm³ dimethylformamide are heated under stirring for 2 hours at 110° C. The solvent is distilled off at reduced pressure, the residue is triturated with water and extracted with chloroform. Chloroform is distilled off and the residual yellow oil (6.19 g.) is heated with 30 cm³ 96% ethanol and 2 g. of DOWEX 50 W synthetic resin under stirring for 8 hours. The solution is filtered and the filtrate is evaporated and recrystallized from ethyl acetate. 4.2 g. (85% yield) of 4-(theophylline-7-yl)-butanol-1 are obtained. M.p.: 114°–116° C.

b. 2.52 g. theophyllinyl-butanol prepared according to Example a, 30 cm³ of benzene and 0.9 cm³ thionyl chloride are heated for 1 hour. The solvent is distilled off and the residual oil crystallizes and thus 2.61 g. (96% yield) of 1-chloro-4-(thiophyllin-7- yl)-butane are obtained, m.p.: 91°–93° C.

c. 2.7 g. of theophylline-chloro-butane according to Example b., 0.51 g. of sodium cyanide, 0.01 g. of sodium iodide and 10 cm³ of dimethylformamide are heated at 95° C. for 5 hours. Thus 1.9 g. (73% yield) of δ-(theophylline-7- yl)-valeronitrile are obtained, m.p.: 118°–120° C. (ethylacetate).

d. One may proceed according to Example 12b and by reacting the nitrile with hydroxyl amine δ-(theophylline-7-yl)-valerianic acid amidoxime are obtained, m.p.: 159°–162° C.

e. 10.0 g. of δ-(theophylline-7-yl)-valerianic acid amidoxime, 2.3 g. of sodium ethylate, 30 cm³ of ethyl acetate and 30 cm³ of ethanol are boiled for 8 hours under stirring. 8.1 g. (75% yield) of 7-[4-(5-methyl-1,2,4-oxadiazol-3-yl)-butan-1-yl]-theophylline are obtained, m.p.: 131°–132° C. (ethanol).

f. 4.0 g. δ-(theophylline-7-yl)-valerianic acid amidoxime, 5.03 g. of β-piperidino-propionic acid ethyl ester, 0,51 g. of sodium methylate, and 70 cm³ of toluene are heated and salt is formed with 1.58 g. of maleic acid. 5.15 g. (91% yield) of 7-{4-[5-(2-piperidinoethan-1-yl)-1,2,4-oxadiazol-3-yl]-butan-1-yl}-theophylline-maleinate are obtained, m.p.: 146°–147° C.

Example 14 a. 16.8 g. of theophylline sodium, 17.2 g. of 2-(5-chloropentane-1-yl-oxy)(-pyrane, 0.5 g. of sodium iodide and 30 cm³ of dimethylformamide are reacted according to Example 13a and 13.5 g. (61% yield) of 5-(theophylline-7yl)-pentanol-1 are obtained, m.p.: 113°–115° C.

b. 13.1 g. of 5-(theophylline-7-yl)-pentanol-1, 60 cm³ of benzene, 3.8 cm³ of thionyl chloride and 0.2 cm³ of pyridine are reacted according to Example 13b and 11.5 g. (93% yield) of 1chloro-5-(theophyllin-7-yl)-pentane are obtained, m.p.: 78°–80° C.

c. 10.0 g. of 1-chloro-5-(theophyllin-7-yl)-pentane, 2.44 g. of potassium cyanide and 40 cm³ of dimethylformamide are reacted according to Example 13c and 7.92 g. (76.5% yield) of 7-(5-cyano-pentan-1-yl)-theophylline are obtained, m.p.: 86°–88° C.

d. This nitrile is reacted with 5.5 g. of hydroxyl amine according to Example 12b and thus 5.2 g. (85% yield) of ε-(theophyllin-7-yl)-hexanoic acid amidoxime are obtained, m.p.: 171°–174° C.

e. 3.08 g. of ε-(theophyllin-7yl)-hexanoic acid amidoxime are dissolved in 10 cm³ acetic anhydride under mild heating and the mixture is then heated on water bath for 3 hours. After cooling 10 cm³ of diethyl ether are added to the precipitated crystal mass, it is filtered by suction and washed with ether. 2.95 g. (93% yield) of 7-[(5-methyl-1,2,4-oxadiazol-3-yl)-pentan-yl]-theophylline are obtained, m.p.: 160°–162° C.

Example 15

9.42 g. of 3-(theophyllin-7-yl)-2-hydroxy-propionic acid amidoxime, are added to the solution of 1.38 g. of metal sodium in 150 cm³ of ethanol and the mixture is heated on water bath for 12 hours and evaporated. Thus 8.5 g. (74% yield) of 7-(2-hydroxy-3-[5-phenyl-1,2,4-oxadiazol-3-yl]-propan-1-yl)-theophylline are obtained, m.p.: 179°–180° C. (ethanol).

Example 16

5.04 g. of 2-(theophylline-7-yl)-acetamidoxime, 2.16 g. of sodium methylate, 4.72 g. of diethyl carbonate and 100 cm³ of toluene are heated for 2 hours to boiling, the mixture is then evaporated and the residue crystallized from water. 4.3 g. (82% yield) of 7-[(5-hydroxy-1,2,4-oxadiazol-3-yl)-methyl]-theophylline are obtained. M.p.: 206°–207° C.

TABLE II

The following table (Examples 17 to 85) shows the new compounds prepared according to Examples 1 to 16 by indicating the A chain, substituent $R_1$, the method, melting point and the acid forming component if necessary

| No. of Example | A | $R_1$ | method | m.p. °C. |
|---|---|---|---|---|
| 17 | $CH_2$ | $CH_2CH_3$ | Example 1.f. | 129–130 |
| 18 | $CH_2$ | —$(CH_2)_2CH_3$ | Example 1.f. | 126–127 |
| 19 | $CH_2$ | —$CH(CH_3)_2$ | Example 1.f. | 125–126 |
| 20 | $CH_2$ | $(CH_2)_2CH_3$ | Example 1.f. | 128–130 |
| 21 | $CH_2$ | —$CH_2CH(CH_3)_2$ | Example 1.f. | 124–125 |
| 22 | $CH_2$ | —$C(CH_3)_3$ | Example 1.f. | 130–132 |
| 23 | $CH_2$ | —$(CH_2)_4CH_3$ | Example 1.f. | 112–114 |
| 24 | $CH_2$ | —$(CH_2)_9CH_3$ | Example 1.f. | 103–105 |
| 25 | $CH_2$ | cyclopentyl | Example 1.f. | 110–111 |
| 26 | $CH_2$ | cyclohexyl | Example 1.f. | 112–113 |
| 27 | $CH_2$ | $CH_2NHCH(CH_3)_2$ | Example 3.a. | 212–213 (hydrochloride) |
| 28 | $CH_2$ | —$CH_2$—N(piperidinyl) | Example 3.a. | 203–206 (hydrochloride) |
| 29 | $CH_2$ | —$(CH_2)_2NHCH(CH_2)_2$ | Example 4.a. | 212–213 (hydrochloride) |
| 30 | $CH_2$ | —$(CH_2)_2$—N(piperidinyl) | Example 4.b. | 96–98 |
| 31 | $CH_2$ | —$(CH_2)_2$—N(piperidinyl) | Example 4.b. | 108–112; 217–218 (hydrochloride) |
| 32 | $CH_2$ | —$(CH_2)_2N(C_2H_5)_2$ | Example 4.b. | 78–80; 127–128 (maleinate) |

TABLE II-continued

The following table (Examples 17 to 85) shows the new compounds prepared according to Examples 1 to 16 by indicating the A chain, substituent $R_1$, the method, melting point and the acid forming component if necessary

| No. of Example | A | $R_1$ | method | m.p. °C. |
|---|---|---|---|---|
| 33 | $CH_2$ | $-(CH_2)_2-N\diagup\diagdown N-CH_3$ (piperazine) | Example 4.b. | 87–89 |
| 34 | $CH_2$ | $(CH_2)_2-N\diagup\diagdown$ (pyrrolidine) | Example 4.b. | 203–204 (hydrochloride) |
| 35 | $CH_2$ | $(CH_2)_2-N\diagup\diagdown$ (piperidine) | Example 4.b. | 206–208 (hydrochloride) |
| 36 | $CH_2$ | $(CH_2)_3N(C_2H_5)_2$ | Example 4.b. | 119–121 (maleinate) |
| 37 | $CH_2$ | p-Cl—$C_6H_4$ | Example 3.a. | 181–183 |
| 38 | $CH_2$ | o-HO—$C_6H_4$ | Example 3.a. | 201–202 |
| 39 | $(CH_2)_2$ | $CH_2CH_3$ | Example 1.f. | 113–114 |
| 40 | $(CH_2)_2$ | $(CH_2)_4CH_3$ | Example 1.f. | 106–108 |
| 41 | $(CH_2)_2$ | —$C_6H_{11}$ (cyclohexyl) | Example 1.f. | 108–109 |
| 42 | $(CH_2)_2$ | —$CH_2Cl$ | Example 2 | 134–138 |
| 43 | $(CH_2)_2$ | $(CH_2)_2Cl$ | Example 4.g. | 140–143 |
| 44 | $(CH_2)_2$ | $(CH_2)_3Cl$ | Example 4.g. | 124–127 |
| 45 | $(CH_2)_2$ | $CH(OH)CH_3$ | Example 1.f. | 129–130 |
| 46 | $(CH_2)_2$ | $CH_2N(C_2H_5)_2$ | Example 3.a. | 203–205 (hydrochloride) |
| 47 | $(CH_2)_2$ | $(CH_2)_2$ | Example 4.a. | 125–127 (maleinate) |
| 48 | $(CH_2)_2$ | $(CH_2)_2N\diagup\diagdown$ (pyrrolidine) | Example 4.a. | 207–210 (hydrochloride) |
| 49 | $(CH_2)_2$ | $(CH_2)_2-N\diagup\diagdown$ (piperidine) | Example 4.a. | 204–205 (hydrochloride) |
| 50 | $(CH_2)_2$ | $(CH_2)_2N\diagup\diagdown O$ (morpholine) | Example 4.a. | 180 (hydrochloride) |
| 51 | $(CH_2)_2$ | $(CH_2)_2N(C_2H_5)_2$ | Example 4.a. | 119–120 (maleinate) |
| 52 | $(CH_2)_2$ | $(CH_2)_2N\diagup\diagdown NCH_3$ (N-methylpiperazine) | Example 4.a. | 165 (di-maleinate) |
| 53 | $(CH_2)_2$ | $(CH_2)_3N\diagup\diagdown$ (piperidine) | Example 4.a. | 203–204 (hydrochloride) |
| 54 | $(CH_2)_2$ | $(CH_2)_3N(C_2H_5)_2$ | Example 4.a. | 200–201 (hydrochloride) |
| 55 | $(CH_2)_2$ | $C_6H_5$ | Example 3.a. | 183–185 |

TABLE II-continued

The following table (Examples 17 to 85) shows the new compounds prepared according to Examples 1 to 16 by indicating the A chain, substituent R₁, the method, melting point and the acid forming component if necessary

| No. of Example | A | R₁ | method | m.p. °C. |
|---|---|---|---|---|
| 56 | $(CH_2)_2$ | p-Cl—$C_6H_4$ | Example 3.a. | 190–191 |
| 57 | $(CH_2)_2$ | o-HO—$C_6H_4$ | Example 3.a. | 202–205 |
| 58 | $(CH_2)_2$ | —OH | Example 1.b. | 205–206 |
| 59 | $(CH_2)_3$ | $CH_3$ | Example 1.d. | 120–122 |
| 60 | $(CH_2)_3$ | cyclohexyl | Example 1.f. | 97–98 |
| 61 | $(CH_2)_3$ | $(CH_2)_2Cl$ | Example 4.g. | 111–112 |
| 62 | $(CH_2)_3$ | $(CH_2)_2N$(piperidinyl) | Example 12.c. | 158–159 (maleinate) |
| 63 | $(CH_2)_3$ | $(CH_2)_2N$(morpholinyl) | Example 12.c. | 134–136 (maleinate) |
| 64 | $(CH_2)_3$ | $(CH_2)_2NHCH(CH_3)_2$ | Example 12.c. | 128–130 (maleinate) |
| 65 | $(CH_2)_3$ | $(CH_2)_2N$(N-methylpiperazinyl)—$CH_3$ | Example 12.c. | 171–172 (di-maleinate) |
| 66 | $(CH_2)$ | $(CH_2)_3N$(piperidinyl) | Example 12.c. | 203–205 (hydrochloride) |
| 67 | $(CH_2)_3$ | OH | Example 16. | 212–214 |
| 68 | $(CH_2)_3$ | $C_6H_5$ | Example 3.a. | 176–178 |
| 69 | $(CH_2)_4$ | $(CH_2)_2N(C_2H_5)_2$ | Example 13.f. | 144–146 (maleinate) |
| 70 | $(CH_2)_5$ | $(CH_2)_2N(C_2H_5)_2$ | Example 13.f. | 148–150 (maleinate) |
| 71 | $CH_2CH(OH)CH_2$ | $CH_2CH_3$ | Example 1.f. | 146–148 |
| 72 | $CH_2CH(OH)CH_2$ | $(CH_2)_2CH_3$ | Example 1.f. | 140–141 |
| 73 | $CH_2CH(OH)CH_2$ | cyclohexyl | Example 1.f. | 133–135 |
| 74 | $CH_2CH(OH)CH_2$ | $(CH_2)_2N(C_2H_5)_2$ | Example 11. | 143 (maleinate) |
| 75 | $CH_2CH(OH)CH_2$ | $(CH_2)_2N$(morpholinyl) | Example 11. | 156–159 (maleinate) |
| 76 | $CH_2CH(OH)CH_2$ | $(CH_2)_2N$(N-methylpiperazinyl)$NCH_3$ | Example 11. | 149–150 (di-maleinate) |
| 77 | $CH_2CH(OH)CH_2$ | $(CH_2)_2NHCH(CH_3)_2$ | Example 11. | 207 (hydrochloride) |
| 78 | $CH_2CH(OH)CH_2$ | o-HO—$C_6H_4$ | Example 3.a. | 206–207 |
| 79 | $CH_2CH(OH)CH_2$ | OH | Example 16. | 200–203 |
| 80 | $CH_2$ | $CH_2$—$C_6H_5$ | Example 3.a. | 142–145 |
| 81 | $(CH_2)_2$ | $CH_2$—$C_6H_5$ | Example 3.a. | 136–138 |

TABLE II-continued

The following table (Examples 17 to 85) shows the new compounds prepared according to Examples 1 to 16 by indicating the A chain, substituent $R_1$, the method, melting point and the acid forming component if necessary

| No. of Example | A | $R_1$ | method | m.p. °C. |
|---|---|---|---|---|
| 82 | $(CH_2)_2$ | $CH_2-CH(C_6H_5)_2$ | Example 3.a. | 181–182 |
| 83 | $(CH_2)_3$ | $CH_2CH(C_6H_5)_2$ | Example 3.a. | 134–135 |
| 84 | $CH_2OH(OH)CH_2$ | $CH_2-C_6H_5$ | Example 3.a. | 146–148 |
| 85 | $(CH_2)_3$ | $CH_2-C_6H_5$ | Example 3.a. | 96–98 |

Example 86

5.04 g. of 2-(theophyllin-7-yl)-acetamidoxime and 1.08 g. of sodium methylate are suspended in 60 cm³ dimethylformamide whereafter a solution of 5.13 g. of theophyllin-7-yl-acetyl chloride in 25 cm³ of dimethylformamide is added dropwise within 15 minutes. The mixture is heated for 1 hour and after adding a small amount of activated charcoal it is filtered while hot and the filtrate is evaporated at reduced pressure. The residue is dissolved in 100 cm³ 0.1N sodium hydrogen carbonate solution while hot and after cooling the crystals are filtered by suction, washed with water and crystallized from 50% aqueous ethanol. Thus 6.6 g. of 3-(theophyllin-7-yl-methyl)-5-(theophylline-7-yl)-methyl-1,2,4-oxadiazole are obtained, m.p.: 271°–272° C.

B. PHARMACEUTICAL COMPOSITIONS

Example 87 a. Tablets

| | |
|---|---|
| 7-[(5-methyl-1,2,4-oxadiazol-3-yl)-methyl]-theophylline | 100.0 g. |
| Corn starch | 130.0 g. |
| Calcium phosphate | 209.0 g. |
| Magnesium stearate | 1.0 g. |
| | 440.0 g. |

The blended components are granulated by methods known per se, 1000 pieces of 440 mg. tablets are compressed, each tablet containing 100 mg. of active ingredient.

b. Injection

| | |
|---|---|
| 7-[{5-(2-diethylamino-ethan-1-yl)-1,2,4-oxadiazol-3-yl}-methyl]-theophylline-maleinate | 200.0 g. |
| distilled water ad | 1000.0 cm³ |

The active ingredient is dissolved in distilled water and treated by method known per se. 1000 pieces of 1 cm³ injection vials are prepared each containing 200 mg. of active ingredient.

c. Depot dragées

| | |
|---|---|
| 7-[(5-methyl-1,2,4-oxadiazol-3-yl)-methyl]-theophylline- | 150.0 g. |
| Carboxy-methyl-cellulose | 300.0 g. |
| Stearic acid | 20.0 g |
| Cellulose acetate phtalate | 30.0 g. |
| | 500.0 g. |

The active ingredient, the carboxymethyl cellulose and stearic acid are blended and granulated with a solution of cellulose acetate phtalate in 200 cm³ ethyl acetate-ethanol and 500 mg. dragées are compressed coated with a 5% aqueous polyvinyl pyrrolidone solution containing sugar by method known per se. All dragées contain 150 mg. of active ingredient.

We claim:

1. A compound of the formula I $$\text{(I)}$$

(structure shown: theophylline moiety linked via chain A to a 1,2,4-oxadiazole ring bearing substituent $R_1$)

or a physiological acceptable addition salt thereof, wherein A stands for straight or branched chain $C_{1-5}$ alkylene or $$-CH_2-CH-CH_2-,$$
$$\phantom{-CH_2-}|$$
$$\phantom{-CH_2-}OH$$

$R_1$ stands for straight or branched chain $C_{1-10}$ alkyl, halogeno-alkyl, hydroxyalkyl, $C_{5-6}$ cycloalkyl, vinyl, 2-ethoxyethyl, carbonylalkyl or aminoalkyl of the formula $$-(CH_2)_n-CH-N\begin{matrix}R_2\\\\R_3\end{matrix}$$
$$\phantom{-(CH_2)_n-}|$$
$$\phantom{-(CH_2)_n-}R$$

wherein R stands for hydrogen or methyl,
n is 0 to 3,
$R_2$ stands for hydrogen or straight or branched chain alkyl,
$R_3$ stands for hydrogen or straight or branched chain alkyl or,
$R_2$ and $R_3$ together with the nitrogen atom may form a 5–6 membered ring, which ring can optionally contain an oxygen or a second nitrogen atom, the latter, optionally substituted by methyl or,
$R_1$ can stand for a phenyl group of the formula $R_4R_5C_6H_3$ wherein
$R_4$ and $R_5$ represent independently hydrogen, chlorine, hydroxy, methoxy, ethoxy, methyl or amino or,
$R_1$ may further stand for hydroxy, in this case the compound of the formula I may exist according to the conditions in the form of tautomers of the formula Ia

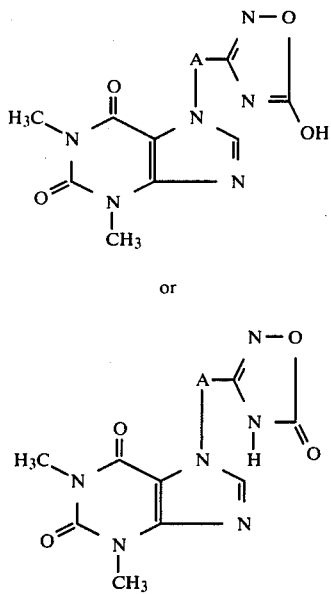

and R₁ may further stand for benzyl, 2,2-diphenylethyl or theophyllin-7-yl-methyl.

2. A compound of the formula I as claimed in claim 1 or an addition salt thereof, wherein A stands for $C_{1-3}$ alkylene or —CH₂—CH—CH₂
R₁ stands for $C_{1-4}$ alkyl or a group of the formula

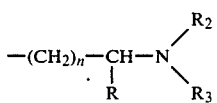

wherein n, R, R₂ and R₃ are as given in claim 1, or hydroxyphenyl or hydroxy.

3. An antitussive pharmaceutical composition comprising as active ingredient a pharmaceutically effective amount of the compound of the Formula (I) as claimed in claim 1 or a physiologically acceptable acid addition salt thereof.

4. A method of treating a cough in a subject susceptible to asthmatic reactions which comprises administering an effective amount of a compound or pharmaceutically effective salt as defined in claim 2 in a dosage form.

5. 7-[(5-methyl-1,2,4-oxidiazol-3-yl)-methyl]-theophylline,

7-[(5-ethyl-1,2,4-oxadiazol-3-yl)-methyl]-theophylline,

7-[5-(propan-2-yl)-1,2,4-oxadiazol-3-yl-methyl]-theophylline,

7-[5-(butan-1-yl)-1,2,4-oxadiazol-3yl-methyl]-theophylline,

7-[{5-(2methyl-propan-1-yl)-1,2,4-oxadiazol-3-yl}-methyl]-theophylline,

7-[{5-(1,1dimethyl-ethan-1-yl)-1,2,4-oxadiazol-3-yl}-methyl]-thoephylline,

7-[{5-(pentan-1-yl)-1,2,4-oxadiazol-3-yl}-methyl]-theophylline,

7-[{5-(decan-1-yl)-1,2,4-oxadiazol-3yl}-methyl]-theophylline,

7-[(5-cyclopentanyl-1,2,4-oxadiazol-3yl)-methyl]-theophylline,

7-[(5-cyclohexanyl-1,2,4-oxadiazol-3-yl)-methyl]-theophylline,

7-[{5-(1-hydroxy-ethan-1-yl)-1,2,4-oxadiazol-3-yl}-methyl]-theophylline,

7-[(5-chloroethyl-1,2,4-oxadiazol-3-yl)-methyl]-theophylline,

7-[{5-(3chloropropan-1-yl)-1,2,4-oxadiazol-3-yl}-methyl]-theophylline,

7-[{5-(butan-3-on-1-yl)-1,2,4-oxadiazol-3-yl}-methyl]-theophylline,

7-[{5-(2-chloroethyl)-1,2,4-oxadiazol-3-yl}-methyl]-theophylline,

7-[{5-(2-ethoxy-ethan-1-yl)-1,2,4-oxadiazol-3-yl}-methyl]-etheophylline,

7-[(5-i.propylaminomethyl-1,2,4-oxadiazol-3-yl)-methyl]-theophylline,

7-[(5diethylaminomethyl-1,2,4-oxadiazol-3-yl)-methyl]-theophylline,

7-[(5-piperidinomethyl-1,2,4-oxadiazol-3-yl)-methyl]-theophylline,

7-[(5-aminomethyl-1,2,4-oxadiazol-3-yl)-methyl]-theophylline,

7-[(5-dimethylaminomethyl-1,2,4-oxadiazol-3-yl)-methyl]-theophylline,

7-[{5-(2-i.-propylamino-ethan-1-yl)-1,2,4-oxadiazol-3-yl}-methyl]-theophylline,

7-[{5-(2-piperidino-ethan-1-yl)-1,2,4-oxadiazol-3-yl}-methyl]-theophylline,

7-[{5-(2-morpholino-ethan-1-yl)-1,2,4-oxadiazol-3-yl}-methyl]-theophylline,

7-[{5-(2-diethylamino-ethan-1-yl)-1,2,4-oxadiazol-3-yl}-methyl]-theophylline,

7-[{5-(2-[N-methyl-piperazino]-ethan-1-yl)-1,2,4-oxadiazol-3-yl}-methyl]-theophylline, 7-[{5-(2-pyrrolidino-ethan-1-yl)-1,2,4-oxadiazol-3-yl}-methyl]-theophylline, 7-[{5-(3-piperidino-propane-1-yl)-1,2,4-oxadiazol-3-yl}-methyl]-theophylline, 7-[5-(3-diethylamino-propan-1-yl-1,2,4-oxadiazol-3-yl)-methyl]-theophylline, 7-[{5-(3-isopropylamino-butan-1-yl)-1,2,4-oxadiazol-3-yl}-methyl]-theophylline, 7-[{5-(4-diethylamino-butan-yl)-1,2,4-oxadiazol-3-yl}-methyl]-theophylline, 7-[(5-phenyl-1,2,4-oxadiazol-3-yl)-methyl]-theophylline, 7-[{5-(4-chlorophenyl)-1,2,4-oxadiazol-3-yl}-methyl]-theophylline, 7-[{5-(2-hydroxyphenyl)-1,2,4-oxadiazol-3-yl}-methyl]-theophylline, 7-[(5-hydroxy-1,2,4-oxadiazol-3-yl)-methyl]-theophylline, 7-[2-(5-methyl-1,2,4-oxadiazol-3-yl)-ethan-1-yl]-theophylline, 7-[2-(5-ethyl-1,2,4-oxadiazol-3-yl)-ethan-1-yl]-theophylline, 7-[2-{5-(pentan-1-yl)-1,2,4-oxadiazol-3-yl}-ethan-1-yl]-theophylline, 7-[2-(5-cyclohexanyl-1,2,4-oxadiazol-3-yl)-ethan-1-yl]-theophylline, 7-[2-{5-(2-chloroethyl)-1,2,4-oxadiazol-3-yl}-ethan-1-yl]-theophylline, 7-[2-(5-chloroethyl-1,2,4-oxadiazol-3-yl)-ethan-1-yl]-theophylline, 7-[2-{5-(3-chloro-propan-1-yl)-1,2,4-oxadiazol-3-yl}-ethan-1-yl]-theophylline, 7-[2-{5-(1-hydroxyethan-1-yl)1,2,4-oxadiazol-3-yl}-ethan-1-yl]-theophylline, 7-[(5-diethylaminomethyl-1,2,4-oxadiazol-3-yl)-ethan-1-yl]-theophylline,
7-[2-{5-(2-isopropylamino-ethan-1-yl)-1,2,4-oxadiazol-3-yl}-ethan-1-yl]-theophylline,
7-[{5-(2-pyrrolidino-ethan-1-yl)-1,2,4-oxadiazol-3-yl}-ethan-1-yl]-theophylline,
7-[2-{5-(2-piperidino-ethan-1-yl)-1,2,4-oxadiazol-3-yl}-ethan-1-yl]-theophylline,
7-[2-{5-(2-morpholino-ethan-1-yl)-1,2,4-oxadiazol-3-yl}-ethan-1-yl]-theophylline,
7-[2-{5-(2-dimethylamino-ethan-1-yl)-1,2,4-oxadiazol-3-yl}-ehtan-1-yl]-theophylline,
7-[2-{5-(2-[N-methyl-piperazino]-ethan-1-yl)-1,2,4-oxadiazol-3-yl}-ethan-1-yl]-theophylline,
7-[2-{5-(3-piperidino-propan-1-yl)-1.2.4-oxadiazol-3-yl}-ethan-1-yl]-theophylline.
7-[2-{5-(3-diethylamino-propan-1-yl)-1,2,4-oxadiazol-3-yl}-ethan-1-yl]-theophylline,
7-[2-(5-phenyl-1,2,4-oxadiazol-3-yl)-ethan-1-yl]-theophylline,
7-[2-(5-hydroxy-1,2,4-oxadiazol-3-yl)-ethan-1-yl]-theophylline,
7-[2-{5-(4-chlorophenyl)-1,2,4-oxadiazol-3-yl}-ethan-1-yl]-theophylline,
7-[2-{5-(2-hydroxypehnyl)-1,2,4-oxadiazol-3-yl}-ethan-1yl]-theophylline,
7-[3-(5-methyl-1,2,4-oxadiazol-3-yl)-propan-1-yl]-theophylline,
7-[3-(5-cyclohexyl-1,2,4-oxadiazol-3-yl)-propan-1-yl]-theophylline,
7-[3-{5-(2-chloroethyl)-1,2,4-oxadiazol-3-yl}-propan-1-yl]-theophylline,
7-[3-{5-(2-piperidino-ethan-1-yl)-1,2,4-oxadiazol-3-yl}-propan-1-yl]-theophylline,
7-[3-{5-(2-diethylamino-ethan-1-yl)-1,2,4-oxadiazol-3-yl}-propan-1-yl]-theophylline,
7-[3-{5-(2-morpholini-ethan-1-yl)-1,2,4-oxadiazol-3-yl}-porpan-1-yl]-theophylline,
7-[3-{5-(2-isopropylamino-ethan-1-yl)-1,2,4-oxadiazol-3-yl}-propan-1-yl]-theophylline,
7-[3-{5-(2-[N-methyl-piperazino]-ethan-1-yl)-1,2,4-oxadiazol-3-yl}-propan-1-yl]-theophylline,
7-[3-{5-(3-piperidino-propan-1-yl)-1,2,4-oxadiazol-3-yl}-propan-1-yl]-theophylline,
7-[3-(5-hydroxy-1,2,4-oxadiazol-3-yl)-propan-1-yl]-theophylline,
7-[3-(5-phenyl-1,2,4-oxadiazol-3-yl)-propan-1-yl]-theophylline,
7-[4-(5-methyl-1,2,4-oxadiazol-3-yl)-butan-1-yl]-theophylline,
7-[4-{5-(2-piperidino-ethan-1-yl)-1,2,4-oxadiazol-3-yl}-butan-1-yl]-theophylline,
7-[4-{5-(2-diethylamino-ethan-1-yl)-1,2,4-oxadiazol-3-yl}-butan-1-yl]-theophylline,
7-[5-(5-methyl-1,2,4-oxadiazol-3-yl)-pentan-1-yl]-theophylline,
7-[5-{5-(2-diethylamino-ethan-1-yl)-1,2,4-oxadiazol-3-yl}-pentane-1-yl]-theophylline,
7-[2-hydroxy-3-(5-methyl-1,2,4-oxadiazol-3-yl)-propane-1-yl]-theophylline,
7-[2-hydroxy-3-(5-ethyl-1,2,4-oxadiazol-3-yl)-propan-1-yl]-theophylline,
7-[2-hydroxy-3-(5-cyclohexyl-1,3,4-oxadiazol-3-yl)-propan-1-yl]-theophylline,
7-[2-hydroxy-3-(5-n-propil-1,2,4-oxadiazol-3-yl-)-propan-1-yl]-theophylline,
7-[2-hydroxy-3-{5-(2-diethylamino-ethan-1-yl)-1,2,4-oxadiazol-3-yl}-propan-1-yl]-theophylline,
7-[2-hydroxy-3-{5-(2-piperidino-ethan-1-yl)-1,2,4-oxadiazol-3-yl}-propan-1-yl]-theophylline,
7-[2-hydroxy-3-{5-(2-morpholino-ethan-1-yl)-1,2,4-oxadiazol-3-yl}-propan-1-yl]-theophylline,
7-[2-hydroxy-3-{5-(2-[N-methyl-piperazino]-ethan-1-yl)-1,2,4-oxadiazol-3-yl-}-propan-1-yl]-theophylline,
7-[2-hydroxy-3-{5-(2-isopropylamino-ethan-1-yl)-1,2,4-oxadiaxol-3-yl}-propan-1-yl]-theophylline,
7-[2-hydroxy-3-(5-phenyl-1,2,4-oxadiazol-3-yl)-propan-1-yl]-theophylline,
7-[2-hydroxy-3-{5-(2-hydroxyphenyl)-1,2,4-oxadiazol-3-yl}-propan-1-yl]-theophylline,
7-[2-hydroxy-3-(5-hydroxy-1,2,4-oxadiazol-3-yl)-propan-1-yl]-theophylline,
7-[5-(benzyl-1,2,4-oxadiazol-3-yl)-nethyl]-theophylline,
7-[2-(5-benzyl-1,2,4-oxadiazol-3-yl-ethan-1-yl]-theophylline,
7-[2-{5-(2,2,-diphenyl-ethan-1-yl)-1,2,4-oxadiazol-3-yl}-ethan-1-yl]-theophylline,
7-[3(5-benzyl-1,2,4-oxadiazol-3-yl)-propan-1-yl]-theophylline,
7-[3-5-(2,2-diphenyl-ethan-1-yl)-1,2,4-oxadiazol-3-yl-propan-1-yl]-theophylline, or
7-[5-(theophyllin-7-yl-methyl)-1,2,4-oxadiazol-3-yl-methyl]-theophylline, or a pharmaceutically effective salt thereof.

6. A process for the preparation of a compound of the Formula (I)

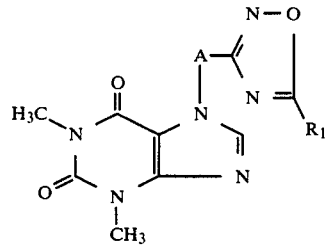

or a physiologically acceptable acid addition salt thereof, wherein A is a straight or branched chain $C_1$–$C_5$ alkylene or

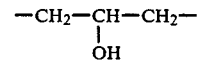

$R_1$ is a straight or branched chain $C_1$–$C_{10}$ alkyl, haloalkyl, hydroxyalkyl, $C_5$–$C_6$ cycloalkyl, vinyl, 2-ethoxyethyl, carbonylalkyl, or aminoalkyl of the Formula

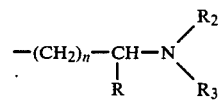

n is 0 to 3;
R is hydrogen or methyl;
$R_2$ is hydrogen or straight or branched chain alkyl;
$R_3$ is hydrogen or straight or branched chain alkyl; or
$R_2$ and $R_3$ together with the adjacent nitrogen atom form a 5- or 6-membered ring, which can optionally contain an oxygen or a second nitrogen atom, the latter optionally substituted by methyl; or
$R_1$ is a phenyl group of the Formula $R_4R_5C_6H_3$ wherein $R_4$ and $R_5$ are independently hydrogen, chlorine, hydroxy, methoxy, ethoxy, methyl or amino or $R_1$ is hydroxy, in which case the compound of the Formula (I) may exist in the form of tautomers of the Formula (Ia)

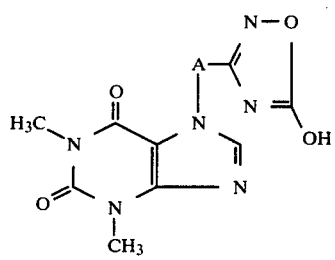

or Ib

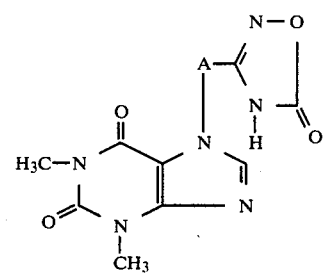

or;

$R_1$ is benzyl, 2,2-diphenylethyl or theophyllin-7-yl-methyl; which comprises the steps of:

(a) acylating a compound of the Formula (II)

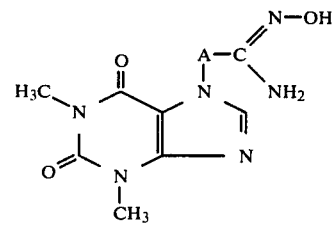

with a compound of the Formula (III)

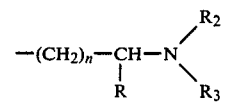

or a corresponding acid anhydride or acid halide, wherein $R_6$ is a $C_1$-$C_{10}$ straight or branched chain alkyl, haloalkyl, hydroxyalkyl, $C_5$-$C_6$ cycloalkyl, vinyl, 2-ethoxyethyl, carbonylalkyl, $C_3$-$C_4$ oxoalkyl, O-tosylalkyl, O-mesylalkyl, or aminoalkyl of the Formula:

$$-(CH_2)_n-\underset{R}{CH}-N\underset{R_3}{\overset{R_2}{\diagdown}}$$

to produce a compound of the Formula (IV)

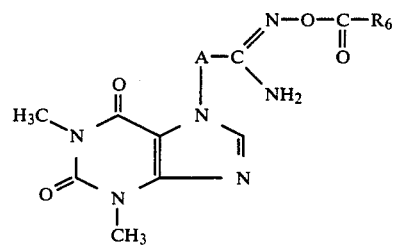

and
(b) with or without isolation of the compound of the Formula (IV) subjecting same to ring closure in an aqueous, or aqueous organic solvent medium at a pH between 6 to 8, to yield the compound of the Formula (I).

* * * * *